United States Patent
Connelly et al.

(10) Patent No.: US 11,065,652 B2
(45) Date of Patent: Jul. 20, 2021

(54) ENDOSCOPE CLEANING STATION HAVING LEAK TESTER AND HIGH-PRESSURE PORT

(71) Applicant: 9485562 Canada Inc., Calgary (CA)

(72) Inventors: Scott Connelly, Calgary (CA); Robert Swayne, Ottawa (CA); Mark Howes, Dalkeith (CA)

(73) Assignee: 9485562 Canada Inc., Canmore (CA)

( * ) Notice: Subject to any disclaimer, the term of this patent is extended or adjusted under 35 U.S.C. 154(b) by 117 days.

(21) Appl. No.: 15/961,405

(22) Filed: Apr. 24, 2018

(65) Prior Publication Data
US 2018/0304315 A1 Oct. 25, 2018

Related U.S. Application Data

(60) Provisional application No. 62/489,896, filed on Apr. 25, 2017.

(51) Int. Cl.
*B08B 3/04* (2006.01)
*A61B 1/12* (2006.01)

(52) U.S. Cl.
CPC ............. *B08B 3/04* (2013.01); *A61B 1/123* (2013.01); *A61B 1/125* (2013.01)

(58) Field of Classification Search
CPC ............. B08B 3/04; A61B 1/125; A61B 1/123
See application file for complete search history.

(56) References Cited

U.S. PATENT DOCUMENTS

| | | |
|---|---|---|
| 5,858,305 A | 1/1999 | Malchesky |
| 6,915,810 B2 | 7/2005 | Weber |
| 8,673,212 B2 | 3/2014 | McDonnell et al. |
| 9,114,185 B2 | 8/2015 | Affaitati |

(Continued)

FOREIGN PATENT DOCUMENTS

| | | |
|---|---|---|
| WO | 0156615 A2 | 8/2001 |
| WO | 2013031388 A1 | 3/2013 |

OTHER PUBLICATIONS

International Search Report & Written Opinion Application No. PCT/CA2018/050477 dated Jul. 12, 2018 14 Pages.

*Primary Examiner* — Benjamin L Osterhout
(74) *Attorney, Agent, or Firm* — Whitmyer IP Group LLC

(57) ABSTRACT

An endoscope cleaning station for cleaning an endoscope includes a sink having an inlet connected to a water supply for filling the sink and a drain for draining the sink, a fill solenoid for controlling a flow of water to the inlet of the sink, a detergent pump and detergent valve that cooperate to selectively dispense detergent into another flow of water thus creating a detergent solution, a manifold for injecting the detergent solution into the endoscope, a lumen solenoid for controlling the flow of the detergent solution to the manifold, a pressure regulator disposed downstream of the lumen solenoid and upstream of the manifold to reduce a pressure of the detergent solution delivered to the manifold, and a high-pressure port connected to a narrow channel of the endoscope, the high-pressure port receiving the detergent solution that bypasses the pressure regulator so that the detergent solution exiting the high-pressure port into the narrow channel has a higher pressure than the pressure of the detergent solution delivered to the manifold.

15 Claims, 3 Drawing Sheets

(56) References Cited

U.S. PATENT DOCUMENTS

| | | | | |
|---|---|---|---|---|
| 2001/0032494 A1* | 10/2001 | Greszler | ............ | A61B 1/00057 |
| | | | | 73/40 |
| 2002/0001537 A1* | 1/2002 | Hlebovy | .................. | A61L 2/18 |
| | | | | 422/28 |
| 2004/0118413 A1* | 6/2004 | Williams | ............... | A61B 1/125 |
| | | | | 128/898 |
| 2007/0100204 A1* | 5/2007 | Feld | .......................... | A61L 2/18 |
| | | | | 600/117 |
| 2010/0022839 A1 | 1/2010 | Onishi et al. | | |
| 2010/0078046 A1* | 4/2010 | Labib | ..................... | A61B 1/123 |
| | | | | 134/22.12 |
| 2013/0023920 A1* | 1/2013 | Terliuc | .................. | A61B 1/015 |
| | | | | 606/192 |
| 2015/0305608 A1 | 10/2015 | Komiya et al. | | |
| 2016/0095508 A1 | 4/2016 | Terliuc et al. | | |
| 2017/0308692 A1* | 10/2017 | Yano | .................... | H04W 4/029 |

\* cited by examiner

```
┌─────────────────────────────────────────────────────────────┐
│ Providing an endoscope cleaning station that comprises a    │
│ sink having an inlet connected to a water supply for        │
│ filling the sink and a drain for draining the sink          │
└─────────────────────────────────────────────────────────────┘
                              ▼
┌─────────────────────────────────────────────────────────────┐
│ Controlling a flow of water to the inlet of the sink using  │
│ a fill solenoid                                             │
└─────────────────────────────────────────────────────────────┘
                              ▼
┌─────────────────────────────────────────────────────────────┐
│ Selectively dispensing detergent into another flow of water │
│ thus creating a detergent solution using a detergent pump   │
│ and detergent valve                                         │
└─────────────────────────────────────────────────────────────┘
                              ▼
┌─────────────────────────────────────────────────────────────┐
│ Injecting the detergent solution into the endoscope using   │
│ a manifold                                                  │
└─────────────────────────────────────────────────────────────┘
                              ▼
┌─────────────────────────────────────────────────────────────┐
│ Controlling the flow of the detergent solution to the       │
│ manifold using a lumen solenoid                             │
└─────────────────────────────────────────────────────────────┘
                              ▼
┌─────────────────────────────────────────────────────────────┐
│ Reducing a pressure of the detergent solution delivered to  │
│ the manifold using a pressure regulator disposed downstream │
│ of the lumen solenoid and upstream of the manifold          │
└─────────────────────────────────────────────────────────────┘
                              ▼
┌─────────────────────────────────────────────────────────────┐
│ Cleaning a narrow channel of the endoscope using a          │
│ high-pressure port configured to be connected to the narrow │
│ channel by receiving the detergent solution at the          │
│ high-pressure port that bypasses the pressure regulator so  │
│ that the detergent solution exiting the high-pressure port  │
│ into the narrow channel has a higher pressure than the      │
│ pressure of the detergent solution delivered to the manifold│
└─────────────────────────────────────────────────────────────┘
```

*FIG. 2*

Providing an endoscope cleaning station that comprises a sink having an inlet connected to a water supply for filling the sink and a drain for draining the sink, a fill solenoid for controlling a flow of water to the inlet of the sink, a detergent pump and detergent valve that cooperate to selectively dispense detergent into another flow of water thus creating a detergent solution, a manifold for injecting the detergent solution into the endoscope, a lumen solenoid for controlling the flow of the detergent solution to the manifold

Connecting an outer sheath of the endoscope to a leak test port of the station

Pressurizing an outer sheath of the endoscope via the leak test port to verify a pressure integrity of the outer sheath of the endoscope

*FIG. 3*

ENDOSCOPE CLEANING STATION HAVING LEAK TESTER AND HIGH-PRESSURE PORT

TECHNICAL FIELD

The present invention relates generally to techniques for cleaning endoscopes and, more particularly, to cleaning stations for cleaning endoscopes.

BACKGROUND OF THE INVENTION

An endoscope is a medical instrument used in endoscopic procedures. Endoscopes are generally long tubes designed to convey inspection and/or surgical equipment into a patient enabling a physician to conduct diagnostic and/or medical/surgical procedures within the patient. Endoscopes are typically designed to be inserted into a patient through the mouth or rectum whereupon they can be conveyed to a location of interest (eg. esophagus or colon) for the purposes of inspecting the inside of a particular body cavity or organ and/or conducting a medical/surgical procedure. After an endoscopic procedure is completed, the endoscope must be cleaned and disinfected/sterilized prior to reuse on another patient. However, as endoscopes are sophisticated pieces of medical equipment often including various combinations of sophisticated lighting, camera, steering and/or surgical equipment, these components of an endoscope are typically sensitive to aggressive cleaning techniques. As such, an endoscope must be cleaned using gentler techniques that do not damage the endoscope but provide a high degree of cleaning as well as repeatable consistency over time. In particular, cleaning of heat-sensitive endoscopes (e.g., gastrointestinal endoscopes, bronchoscopes, nasopharygoscopes) is particularly challenging because these cannot be sterilized in an autoclave which is the standard cleaning technique for other types of surgical equipment.

Conventionally, cleaning heat-sensitive endoscopes is performed manually by hospital staff. It is common for hospital staff to wipe the endoscope with a detergent, soak it in a water-detergent mixture and then flush it with the same or a different detergent and water before drying the endoscope. Even with rigorous hospital cleaning protocols, infections due to contaminated endoscopes have been reported. It is therefore highly desirable to provide improved techniques for cleaning endoscopes and particularly cleaning techniques that are substantially automated and provide a high degree of consistency.

SUMMARY OF THE INVENTION

In accordance with the invention, embodiments of endoscope cleaning systems and methods of cleaning endoscopes are described.

In a first aspect, an endoscope cleaning station that facilitates the cleaning of endoscopes is described. This cleaning station is primarily used in conjunction with a subsequent sterilization or disinfection step and also a final drying step, which steps may be performed at separate stations.

In one aspect an endoscope cleaning station is described for cleaning an endoscope, wherein the cleaning station includes a sink having an inlet connected to a water supply for filling the sink and a drain for draining the sink. The station includes a fill solenoid for controlling a flow of water to the inlet of the sink. The station includes a detergent pump and detergent valve that cooperate to selectively dispense detergent into another flow of water thus creating a detergent solution. The station also has a manifold for injecting the detergent solution into the endoscope and a lumen solenoid for controlling the flow of the detergent solution to the manifold. A pressure regulator is disposed downstream of the lumen solenoid and upstream of the manifold to reduce a pressure of the detergent solution delivered to the manifold. The station further includes a high-pressure port configured to be connected to a narrow channel of the endoscope. The high-pressure port receives the detergent solution that bypasses the pressure regulator so that the detergent solution exiting the high-pressure port into the narrow channel has a higher pressure than the pressure of the detergent solution delivered to the manifold.

In another aspect, a method of cleaning an endoscope is described, the method including the steps of providing an endoscope cleaning station that comprises a sink having an inlet connected to a water supply for filling the sink and a drain for draining the sink, controlling a flow of water to the inlet of the sink using a fill solenoid, and selectively dispensing detergent into another flow of water thus creating a detergent solution using a detergent pump and detergent valve. The method further entails steps of injecting the detergent solution into the endoscope using a manifold, controlling the flow of the detergent solution to the manifold using a lumen solenoid, and reducing a pressure of the detergent solution delivered to the manifold using a pressure regulator disposed downstream of the lumen solenoid and upstream of the manifold. The method further entails a step of cleaning a narrow channel of the endoscope using a high-pressure port configured to be connected to the narrow channel by receiving the detergent solution at the high-pressure port that bypasses the pressure regulator so that the detergent solution exiting the high-pressure port into the narrow channel has a higher pressure than the pressure of the detergent solution delivered to the manifold.

In a further aspect, an endoscope cleaning station for cleaning an endoscope is described. The station comprises a sink having an inlet connected to a water supply for filling the sink and a drain for draining the sink, a fill solenoid for controlling a flow of water to the inlet of the sink, and a detergent pump and detergent valve that cooperate to selectively dispense detergent into another flow of water thus creating a detergent solution. The station also includes a manifold for injecting the detergent solution into the endoscope. A lumen solenoid is provided for controlling the flow of the detergent solution to the manifold. A leak test port connects to the endoscope to pressurize an outer sheath of the endoscope.

In a further aspect, a method of cleaning an endoscope is described, the method entails providing an endoscope cleaning station that comprises a sink having an inlet connected to a water supply for filling the sink and a drain for draining the sink, a fill solenoid for controlling a flow of water to the inlet of the sink, a detergent pump and detergent valve that cooperate to selectively dispense detergent into another flow of water thus creating a detergent solution, a manifold for injecting the detergent solution into the endoscope, a lumen solenoid for controlling the flow of the detergent solution to the manifold, connecting an outer sheath of the endoscope to a leak test port of the station, and pressurizing the outer sheath of the endoscope via the leak test port to verify a pressure integrity of the outer sheath of the endoscope.

BRIEF DESCRIPTION OF THE DRAWINGS

These and other features of the disclosure will become more apparent from the description in which reference is made to the following appended drawings."

FIG. 2 is a flowchart depicting steps of a method of cleaning an endoscope using a cleaning station having a high-pressure port.

FIG. 3 is a flowchart depicting steps of another method of cleaning an endoscope using a cleaning station having a leak test port.

DETAILED DESCRIPTION OF EMBODIMENTS

Figure 1:
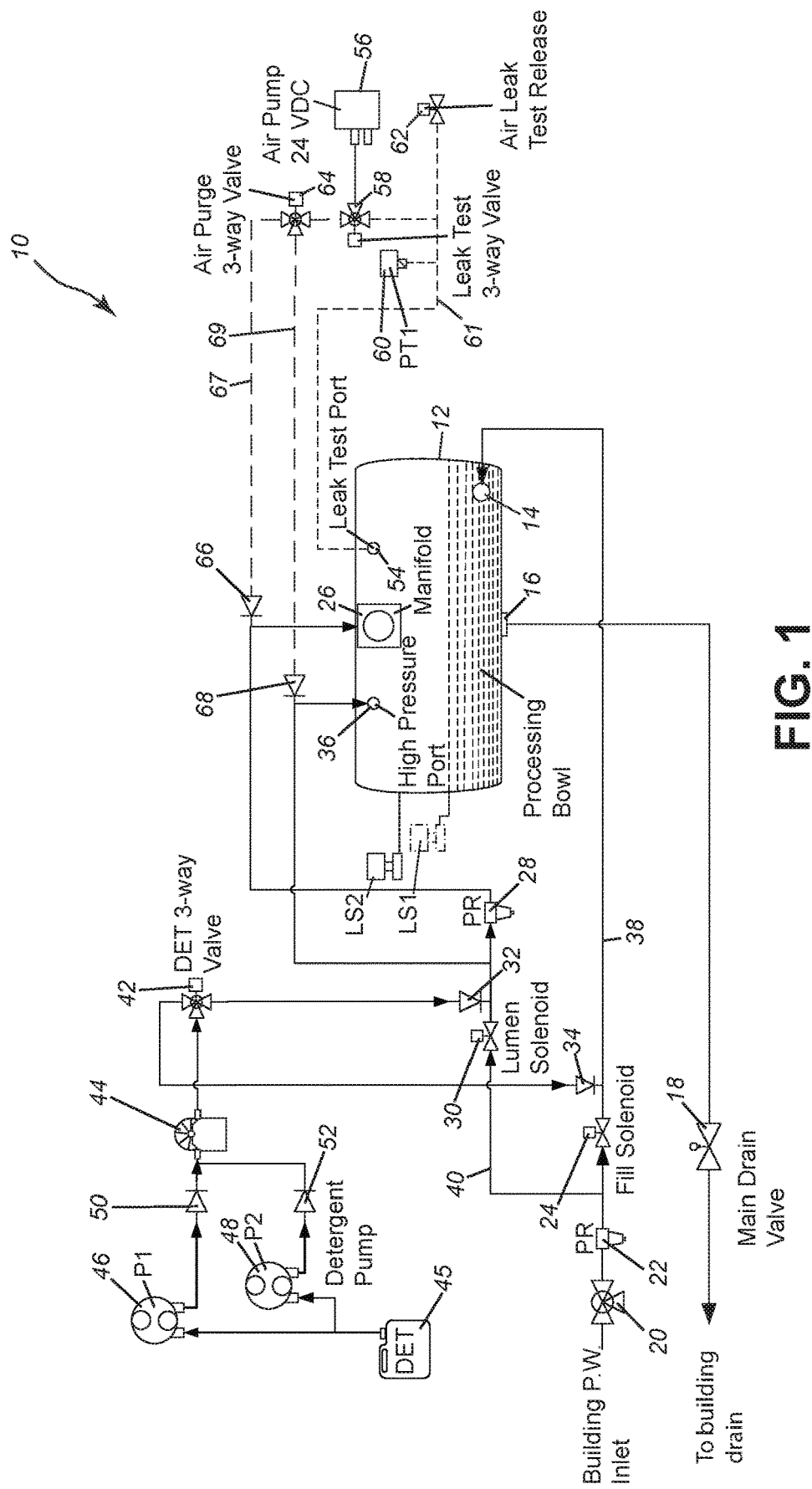
FIG. 1 is a schematic depiction of an endoscope cleaning station in accordance with an embodiment of the present invention.

The following detailed description contains, for the purposes of explanation, numerous specific embodiments, implementations, examples and details in order to provide a thorough understanding of the invention. It is apparent, however, that the embodiments may be practiced without these specific details or with an equivalent arrangement. In other instances, some well-known structures and devices are shown in block diagram form in order to avoid unnecessarily obscuring the embodiments of the invention.

An exemplary embodiment of the novel endoscope cleaning station is depicted schematically in FIG. 1. This cleaning station depicted schematically by way of example in FIG. 1 assists in the manual cleaning of flexible endoscopes prior to disinfection. It should be understood that this exemplary embodiment represents only one way of implementing this technology. In other words, many variations, modifications and refinements may be made to the system presented herein without departing from the fundamental inventive concept(s).

In the embodiment shown by way of example in FIG. 1, an endoscope cleaning station is generally designated by reference numeral 10. The endoscope cleaning station may also be referred to an endoscope cleaning system or apparatus. This cleaning station 10 may be used in conjunction with a disinfecting/sterilization station and a drying station. As shown by way of example in FIG. 1, the endoscope cleaning station 10 includes a sink (or "processing bowl") which may be a stainless steel sink 12, tub or any other open liquid-containing vessel into which an endoscope may be placed for cleaning. Although the sink in the illustrated embodiment is made of stainless steel, other suitable or equivalent materials may be employed. The sink may have a volume sufficient to receive at least approximately 25 liters. However, it will be appreciated that any other suitable volume may be used to clean the endoscope.

The sink 12 has a water inlet 14 connected to a water supply or water line, e.g. a building/hospital pressurized water source. The sink also includes a drain 16 at the bottom of the sink for draining liquid from the sink. The sink is connected to a building/hospital drain. Between the drain 16 and the building drain is a main drain valve 18. Between the building pressurized water inlet and the water inlet 14 of the sink 16 are, in a direction of flow, a mixing valve 20 followed downstream by a first pressure regulator 22 followed downstream by a fill solenoid 24. The mixing valve 20 enables the correct temperature of the water to be achieved which is important to ensure optimal behavior of the enzymatic detergent. Optionally, the water temperature may be microprocessor-controlled using a temperature sensor in the water to provide a feedback signal to the solenoids or other actuators that actuate the hot and cold water intake valves.

As shown by way of example in FIG. 1, the endoscope cleaning station 10 includes a first level sensor LS1 (e.g. "fill-level sensor") and a second level sensor LS2 (e.g. "high level sensor") which each are capable of sensing the level of the liquid in the sink. When LS1 is triggered, this provides a signal to a microcontroller or microprocessor to activate the fill solenoid 24 to stop the flow of water into the sink. LS2 provides a fail-safe in the event that LS1 fails to activate, in which case LS2 will provide a similar signal to stop the flow of water to the sink and prevent an overfill situation. In one example, the desired fill level corresponds to 25 liters although it will be appreciated that this fill level is merely one example and that any other suitable fill levels may be used in other embodiments or variants. In a variant, the drain may be actuated in response to detecting that a fill level has been reached by LS1 or LS2.

As shown by way of example in FIG. 1, the sink 16 includes a manifold 26 that receives low-pressure water or a mixture of detergent and low-pressure water. The low-pressure water is received via a second pressure regulator 28 that reduces the pressure of the water flowing through it. Upstream of the second pressure regulator 28 is a lumen solenoid 30 that can be actuated to control the flow of water into the manifold. The manifold 26 connects to the internal lumens of one or more endoscopes via appropriate connectors to irrigate and flush the internal lumens of the one or more endoscopes being cleaned. Typically, one endoscope will have 2-6 lumens (usually 2-3 lumens) that can be individually connected to the manifold. In most circumstances, a single endoscope will be cleaned at a time but depending on the number of manifold ports and the number of lumens in an endoscope, it would be possible to connect and clean the lumens of multiple endoscopes at one time.

Detergent can be mixed with the water immediately downstream of the lumen solenoid using a non-return valve 32. The resulting mixture of detergent and water flows to the manifold 26. Detergent can also be mixed into the water flowing into the inlet 14 using another non-return valve 34 that is disposed immediately downstream of the fill solenoid. The detergent may be, for example, any suitable enzymatic detergent.

As shown by way of example in FIG. 1, the sink 16 includes a high-pressure port 36 whose purpose is to clean a narrow channel of the endoscope such as an elevator wire channel (that surrounds the elevator wire) or an auxiliary water channel (which is used to wash the endoscopic field of view). This port 36 receives high-pressure water or a water-detergent mixture from a conduit (e.g. tube or supply line) that bypasses the second pressure regulator 28. The water for the high-pressure port 36 derives from the building inlet, flows through the mixing valve and the first pressure regulator. Between the first pressure regulator 22 and the fill solenoid 24, the conduit bifurcates into a first conduit 38 that supplies water to the inlet of the sink and a second conduit 40 that leads to the lumen solenoid. If the lumen solenoid is closed, the flow is blocked to the high-pressure port and manifold. If the lumen solenoid is open, the water flows past the non-return valve, mixing with detergent passing through the non-return valve 32 if a detergent valve 42 is open. Downstream of the non-return valve 32 there is another bifurcation, dividing the flow into a low-pressure flow (regulated by the second pressure regulator 28) to the manifold and a high-pressure flow that bypasses the second pressure regulator 28. The high-pressure flow leads to the high-pressure port 36.

As shown by way of example in FIG. 1, the detergent valve 42 may be a three-way valve providing three positions: off, flow toward manifold, and flow toward inlet. In the off position, there is no detergent flowing or mixing with the water. This position is maintained when it is desired to rinse or flush the endoscope with only water, e.g. to remove the detergent at the end of the cleaning process. In the flow-toward-manifold position, the valve 42 directs the detergent to the non-return valve immediately downstream of the lumen solenoid. In the flow-toward-inlet position, the valve 42 directs the detergent to the non-return valve immediately downstream of the fill solenoid. The detergent is supplied to the three-way detergent valve 42 via a flow meter 44. The detergent is pumped from a detergent container 45 (or detergent source) by one or more detergent pumps 46, 48 through respective non-return valves 50, 52 through the flow meter 44 to the detergent valve 42. In a variant, there may be only a single pump. In another variant, the pumps may pump two different types of detergent from two different containers. The pumps enable automatic and precise mixing of the enzymatic detergent to achieve the optimal concentration.

As shown by way of example in FIG. 1, the sink also includes a leak test port 54 which is connected to a pressurized air system that has an air pump 56 for generating the air pressure needed to perform the leak test. The air pump 56 supplies the pressurized air through a leak test three-way valve 58. When open to the leak test port, pressurized air flows to the leak test port and pressurizes the endoscope attached to the port. A pressure transducer 60 is disposed along the line 61 from the leak test three-way valve 58 to the leak test port to measure the pressure in the line. Also connected to the leak test three-way valve 58 is an air leak test release valve 62. When this valve is opened the pressure in the line is dissipated. This valve must be closed to run the leak test. The leak test three-way valve 58 is also connected to another three-way valve 64, namely an air purge three-way valve. The valve 58 can direct pressurized air to the valve 64 to purge the manifold or the high-pressure port via first and second air lines. A non-return valve 66 is connected at the end of the first air line 67 to a conduit leading to the manifold. Another non-return valve 68 is connected at the end of the second air line 69 to the conduit leading to the high-pressure port.

The station also includes a memory coupled to the microprocessor for storing a record of steps performed for each uniquely identified endoscope. The microprocessor and memory also cooperate with a touch screen display to present onscreen training and an onscreen user manual, troubleshooting, diagnostics, etc. The station can also provide instructions for all non-automated (manual) steps in the cleaning process, e.g. wiping, moving the elevator wire channel. In addition, the station is able to run different processes for different types of endoscopes. Entering an endoscope's unique identifier enables the microprocessor and memory to identify the type of endoscope and the cleaning profile that is required by the hospital.

Methods of Cleaning

Methods of cleaning an endoscope using this cleaning station are described with reference to FIGS. 2 and 3. Initially, before the cleaning method begins, the cleaning station resets all values to zero (e.g. timers, decimal values, etc.). The leak test connector of the endoscope is connected to the leak test port of the sink which, at this point, contains no fluid. The operator enters a user ID and endoscope ID on a user interface (e.g. a touch screen on the sink). The cleaning process thus begins. The leak test release valve activates and opens, releasing any residual pressure inside the endoscope. If the pressure, measured by the leak test pressure transducer, does not drop below a predetermined value the cycle will fail. If after three seconds the pressure is at an acceptable level, the leak test release valve is deactivated and the air pump turns on to pressurize the endoscope's sheath until the inflation value (e.g. 6 psi or any other suitable pressure) has been reached and continues to inflate for a period afterwards, e.g. 10 seconds afterwards. The air pump then turns off and the analogue input leak test pressure transducer is monitored for stability. If the pressure monitored drops below the low alarm value within the testing period the cycle will fail. If the pressure remains above the low alarm value for 40 seconds the leak test is deemed as a pass. The integrity of the outer sheath of the endoscope is thus considered to be safe for further use. Whilst the high level sensor LS1 and the fill sensor LS2 are not on, the water fill solenoid for the bowl/sink is activated. If at any time the high level sensor LS1 activates for more than 2 seconds the microprocessor of the cleaning station will trigger an alarm. When the fill level sensor LS2 activates, the fill solenoid is deactivated. There is also a maximum time in which the sink may continue to fill which safeguards against faulty sensors to prevent overfilling. If all criteria for timings are met and correct, the next step is performed. In this next step, the cleaning station informs the operator/user via the screen to move the distal tip of the endoscope and visually inspect it for small streams of bubbles. When the operator is satisfied with the endoscope's integrity, the operator/user presses the "PASS" button on the touch screen. If the operator observes any air bubbles, then the operator should press the "FAIL" button on the touch screen. Receiving user input signifying that bubbles are observable causes the cycle to fail.

To ensure that there is sufficient space for the mixture of detergent and water in the sink, a small amount of water is drained out. The drain valve is activated for a predetermined period of time based on the sink's drain performance and then deactivated when the predetermined period of time has elapsed. The endoscope is then placed into the sink and its lumens are connected to the ports on the manifold of the sink.

Whilst the analogue flow meter is reading below the required amount of detergent, the first detergent pump 46 (e.g. peristaltic pump) and the detergent three-way valve 42 are activated. The correct amount of detergent is determined by individual chemistry and provided as a variable to the microprocessor of the cleaning station. When the correct amount of detergent is reached, the first detergent pump 46 and the detergent three-way valve 42 are deactivated. If the correct amount of detergent is not dispensed in a predetermined time, the touch screen will display "CHECK AND CHANGE THE DETERGENT BOTTLE" and will invite the operator to press the "TRY AGAIN" button to reach the target amount of detergent. In such a case the process starts over from the beginning. If after three attempts the amount of detergent is not reached, the cycle will fail. If the correct amount of detergent is dispensed, the method may proceed to the next step.

Whilst the high level sensor LS1 and the fill level sensor LS2 are not on, the water fill solenoid is activated for a predetermined time (based on the water pressure of the building or hospital). This is to ensure that the detergent is mixed in the bowl/sink. The time is by default three seconds although this time may be varied. If at any time the high level sensor LS1 activates for more than two seconds the sink will trigger an alarm. If the fill level sensor LS2 activates, the fill solenoid is deactivated. There is also a maximum time in which the sink may continue to fill which is intended to catch faulty sensors to prevent floods and overfills. If all criteria for timings are met and correct, the next step is performed in which detergent solution is injected into the lumens.

Whilst the analogue flow meter is reading below the required amount of detergent for the lumen, the second detergent pump 48 (e.g. peristaltic pump) and the detergent three-way valve 42 and the lumen solenoid 30 are activated. The second pump 48 is controlled also via a programmable logic controller's internal clock frequency which pulses the pump allowing for even distribution of the detergent into the stream of water. The PLC may be the microcontroller or microprocessor referred to earlier or it may be a separate PLC. The correct amount of detergent is determined by individual chemistry and provided as a variable to the PLC or microprocessor. When the correct amount of detergent is reached, the second detergent pump 48, the detergent three-way valve 42 and the lumen solenoid 30 are deactivated. If the correct amount of detergent is not dispensed in a predetermined time, the touch screen will display "CHECK AND CHANGE THE DETERGENT BOTTLE" and will invite the operator to press the "TRY AGAIN" button to reach the target amount of detergent. In such a case the process starts over from the beginning. If after three attempts the amount of detergent is not reached, the cycle will fail. If the correct amount of detergent is dispensed, the method may proceed to the soaking stage.

During the soaking stage, no operator input or action is required. The station remains inactive while the endoscope soaks in the detergent solution. Once the soaking time has elapsed, the method proceeds to the washing step.

During the washing step, whilst the analogue flow meter is reading below the required amount of detergent for the lumen, the second detergent pump 48 (e.g. peristaltic pump) and the detergent three-way valve 42 and the lumen solenoid 30 are activated. The second pump 48 is controlled also via a programmable logic controller's internal clock frequency which pulses the pump allowing for even distribution of the detergent into the stream of water. When both the correct amount of detergent has been dispensed and the wash time has been reached, the second detergent pump 48, the detergent three-way valve 42 and the lumen solenoid 30 are deactivated. If the correct amount of detergent is not dispensed in a predetermined time, the touch screen will display "CHECK AND CHANGE THE DETERGENT BOTTLE" and will invite the operator to press the "TRY AGAIN" button to reach the target amount of detergent. In such a case the process starts over from the beginning. If after three attempts the amount of detergent is not reached, the cycle will fail. If the correct amount of detergent has been dispensed, the microprocessor of the cleaning station verifies that the fill level sensor was activated for at least three seconds between the lumen injection step and the washing step. Activation of the fill level sensor indicates that fluid has flowed through the lumens of the endoscope. Only once this verification has been performed may the method proceed to the draining stage.

In the draining stage, the drain valve and air pump are activated for a predetermined amount of time based on the sink's drain performance. In the subsequent rinsing stage, whilst the high level sensor LS1 and the fill level sensor LS2 are not on, the fill solenoid and the lumen solenoid are activated. If at any time the high level sensor activates for more than two seconds, the station will trigger an alarm. When the fill level sensor LS2 activates, the fill solenoid and the lumen solenoid are deactivated. Once the sink is full the touch screen displays a message to prompt the operator to wipe the exterior of the endoscope and to press the "CON-TINUE" button when finished wiping. As noted above, there is a maximum time allowed for filling in case the sensors fail. If all criteria for timings and wiping are met, the method proceeds to another drain step in which the drain valve and air pump are activated for a predetermined period of time. In a final step, designated the sud rinse, the fill solenoid and the drain valve are activated for a predetermined period of time (e.g. the default being three seconds). Once this time has elapsed, the fill solenoid is deactivated. Another timer starts setting a predetermined time during which the drain valve remains open in order to rid the sink of water, thereby rinsing any remaining suds from the bottom of the sink. The drain valve is then closed after the predetermined time has elapsed. The touch screen then displays "CYCLE COMPLETE". The touch screen may optionally display a button enabling the operator to repeat the rinse step should there be any remaining suds on the bottom of the sink. The station may also display a "FINISH" button to end the cleaning cycle. The endoscope is then disconnected from the high pressure port and the leak test port. The endoscope can then be moved to an automated endoscope reprocessor (AER) for sterilization.

It should be understood that the endoscope cleaning station 10 depicted in FIG. 1 is presented by way of example only. This particular design of the station is believed to be the best mode of implementing the present invention but it should be appreciated that many variations in the system may be made without departing from the inventive concept(s) presented herein.

It is to be understood that the singular forms "a", "an" and "the" include plural referents unless the context clearly dictates otherwise. Thus, for example, reference to "a device" includes reference to one or more of such devices, i.e. that there is at least one device. The terms "comprising", "having", "including" and "containing" are to be construed as open-ended terms (i.e., meaning "including, but not limited to,") unless otherwise noted. All methods described herein can be performed in any suitable order unless otherwise indicated herein or otherwise clearly contradicted by context. The use of examples or exemplary language (e.g. "such as") is intended merely to better illustrate or describe embodiments of the invention and is not intended to limit the scope of the invention unless otherwise claimed.

While several embodiments have been provided in the present disclosure, it should be understood that the disclosed systems and methods might be embodied in many other specific forms without departing from the scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the inventive concept(s) disclosed herein.

The invention claimed is:

1. An endoscope cleaning station for cleaning an endoscope, the station comprising:
   a sink having an inlet connected to a water supply for filling the sink and a drain for draining the sink;
   a fill solenoid for controlling a flow of water to the inlet of the sink;
   a detergent pump and detergent valve that cooperate to selectively dispense detergent into another flow of water thus creating a detergent solution;
   a manifold for injecting the detergent solution into the endoscope;
   a lumen solenoid for controlling the flow of the detergent solution to the manifold;
   a pressure regulator disposed downstream of the lumen solenoid and upstream of the manifold to reduce a pressure of the detergent solution delivered to the manifold; and,
   a high-pressure port configured to be connected to a narrow channel of the endoscope, the high-pressure port receiving detergent solution that bypasses the pressure regulator via a conduit so that the detergent solution exiting the high-pressure port into the narrow channel has a higher pressure than the pressure of the detergent solution delivered to the manifold.

2. The endoscope cleaning station according to claim 1 further including a fill level sensor for sensing a fill level in the sink to control the fill solenoid.

3. The endoscope cleaning station according to claim 2 further including a high level sensor for detecting an overfill condition in the sink and for triggering an alarm if the overfill condition persists.

4. The endoscope cleaning station according to claim 1 further including a high level sensor for detecting an overfill condition in the sink and for triggering an alarm if the overfill condition persists.

5. The endoscope cleaning station according to claim 1 wherein the detergent valve is a three-way detergent valve capable of directing detergent into the flow of water to the inlet of the sink.

6. The endoscope cleaning station according to claim 1 further including a microprocessor coupled to a memory for storing a record of steps performed for each uniquely identified endoscope.

7. An endoscope cleaning station for cleaning an endoscope, the station comprising:
   a sink having an inlet connected to a water supply for filling the sink and a drain for draining the sink;
   a fill solenoid for controlling a flow of water to the inlet of the sink;
   a detergent pump and detergent valve that cooperate to selectively dispense detergent into another flow of water thus creating a detergent solution;
   a manifold for injecting the detergent solution into the endoscope;
   a lumen solenoid for controlling the flow of the detergent solution to the manifold;
   a leak test port configured to be connected to the endoscope; and
   an air pump and a leak test three-way valve connected to the air pump for selectively distributing pressurized air to the leak test port for pressurizing an outer sheath of the endoscope and an air purge three-way valve capable of diverting pressurized air to purge either the manifold or a high-pressure port.

8. The endoscope cleaning station according to claim 7 further including a pressure transducer for measuring air pressure.

9. The endoscope cleaning station according to claim 7 further including a leak test release valve.

10. The endoscope cleaning station according to claim 7 further comprising a pressure regulator disposed downstream of the lumen solenoid and upstream of the manifold to reduce a pressure of the detergent solution delivered to the manifold.

11. The endoscope cleaning station according to claim 10 further comprising a high-pressure port configured to be connected to a narrow channel of the endoscope, the high-pressure port receiving detergent solution that bypasses the pressure regulator via a conduit so that the detergent solution exiting the high-pressure port into the narrow channel has a higher pressure than the pressure of the detergent solution delivered to the manifold.

12. The endoscope cleaning station according to claim 7 further including a fill level sensor for sensing a fill level in the sink to control the fill solenoid.

13. The endoscope cleaning station according to claim 7 further including a high-level sensor for detecting an overfill condition in the sink and for triggering an alarm if the overfill condition persists.

14. The endoscope cleaning station according to claim 7 wherein the detergent valve is a three-way detergent valve capable of directing detergent into the flow of water to the inlet of the sink.

15. The endoscope cleaning station of according to claim 7 further including a microprocessor coupled to a memory for storing a record of steps performed for each uniquely identified endoscope.

* * * * *